(12) United States Patent
Shalon et al.

(10) Patent No.: US 8,449,448 B2
(45) Date of Patent: May 28, 2013

(54) FECAL INCONTINENCE DEVICE, SYSTEMS AND METHOD

(75) Inventors: Tidhar Shalon, Palo Alto, CA (US); Guy Kotlizky, Kfar-Shemaryahu (IL)

(73) Assignee: Renew Medical, Inc., Palo Alto, CA (US)

( * ) Notice: Subject to any disclaimer, the term of this patent is extended or adjusted under 35 U.S.C. 154(b) by 0 days.

(21) Appl. No.: 13/546,887

(22) Filed: Jul. 11, 2012

(65) Prior Publication Data

US 2012/0277523 A1  Nov. 1, 2012

Related U.S. Application Data

(63) Continuation of application No. 12/376,294, filed as application No. PCT/IL2008/001450 on Nov. 5, 2008.

(60) Provisional application No. 61/064,374, filed on Feb. 29, 2008, provisional application No. 60/996,275, filed on Nov. 8, 2007.

(51) Int. Cl.
    *A61F 2/02* (2006.01)
(52) U.S. Cl.
    USPC ............................. 600/30; 600/29; 128/887
(58) Field of Classification Search
    USPC ............... 600/29–32; 604/332–337; 128/887
    See application file for complete search history.

(56) References Cited

U.S. PATENT DOCUMENTS

| 3,127,893 | A |   | 4/1964  | Montague |
|-----------|---|---|---------|----------|
| 3,447,533 | A | * | 6/1969  | Spicer ............................ 600/32 |
| 3,570,489 | A |   | 3/1971  | Brown |
| 3,841,304 | A |   | 10/1974 | Jones |
| 4,563,182 | A |   | 1/1986  | Stoy et al. |
| 4,686,985 | A |   | 8/1987  | Lottick |
| 5,417,226 | A |   | 5/1995  | Juma |
| 5,482,039 | A |   | 1/1996  | Place |
| 5,513,659 | A |   | 5/1996  | Buuck et al. |
| 5,749,826 | A |   | 5/1998  | Faulkner |
| 6,096,057 | A |   | 8/2000  | Klingenstein |
| 6,364,852 | B1 |  | 4/2002  | Lee |
| 6,440,060 | B1 |  | 8/2002  | Latour, Jr. |
| 6,468,245 | B2 |  | 10/2002 | Alexandersen |
| 6,471,635 | B1 |  | 10/2002 | Forsell |
| 6,485,476 | B1 |  | 11/2002 | von Dyck et al. |
| 6,749,556 | B2 |  | 6/2004  | Banik |
| 6,907,293 | B2 |  | 6/2005  | Grill et al. |

(Continued)

FOREIGN PATENT DOCUMENTS

| CA | 2136318 A1 | 12/1993 |
| EP | 0188376 A1 | 7/1986 |

(Continued)

OTHER PUBLICATIONS

International search report dated Jun. 26, 2009 for PCT Application No. IL09/00224.

(Continued)

*Primary Examiner* — Patricia Bianco
*Assistant Examiner* — Keri J Nelson
(74) *Attorney, Agent, or Firm* — Wilson, Sonsini, Goodrich & Rosati

(57) ABSTRACT

A device for treating fecal incontinence in a subject is provided. The device includes a plug configured for positioning mostly within an anal canal of the subject.

9 Claims, 9 Drawing Sheets

U.S. PATENT DOCUMENTS

| | | |
|---|---|---|
| 6,929,663 B2 | 8/2005 | Rioux et al. |
| 7,054,689 B1 | 5/2006 | Whitehurst et al. |
| 7,455,690 B2 | 11/2008 | Cartledge et al. |
| 7,553,273 B2 | 6/2009 | Ferguson |
| 7,695,489 B2 | 4/2010 | Brockman |
| 2003/0032857 A1 | 2/2003 | Forsell |
| 2004/0267198 A1 | 12/2004 | Torstensen |
| 2007/0287968 A1 | 12/2007 | Daneshvar |
| 2010/0152529 A1 | 6/2010 | Shalon et al. |
| 2012/0190915 A1 | 7/2012 | Shalon et al. |
| 2012/0277522 A1 | 11/2012 | Shalon et al. |
| 2013/0006046 A1 | 1/2013 | Shalon et al. |

FOREIGN PATENT DOCUMENTS

| | | |
|---|---|---|
| EP | 0334509 A2 | 9/1989 |
| EP | 0422693 A2 | 4/1991 |
| EP | 0850657 A1 | 7/1998 |
| WO | WO 2006/047833 A1 | 5/2006 |
| WO | WO 2007/077551 A2 | 7/2007 |
| WO | WO 2007/077551 A3 | 10/2007 |

OTHER PUBLICATIONS

International search report dated Mar. 6, 2009 for PCT Application No. IL2008/001450.

McMahon, et al. Three-dimensional biomechanical properties of the human rectum evaluated with magnetic resonance imaging. Neurogastroenterol Motil. Aug. 2005;17(4):531-40.

Vaizey, et al. Injectable bulking agents for treating faecal incontinence. Br J Surg. May 2005;92(5):521-7.

Written opinion dated Jun. 26, 2009 for PCT Application No. IL09/00224.

Written opinion dated Mar. 6, 2009 for PCT Application No. IL2008/001450.

Office action dated Apr. 24, 2012 for U.S. Appl. No. 12/376,294.

Office action dated Sep. 26, 2012 for U.S. Appl. No. 13/546,879.

Office action dated Oct. 11, 2011 for U.S. Appl. No. 12/376,294.

Office action dated Nov. 9, 2012 for U.S. Appl. No. 13/546,898.

European search report dated Nov. 22, 2012 for EP Application No. 08828891.5.

European search report dated Nov. 22, 2012 for EP Application No. 11170858.2.

* cited by examiner

FECAL INCONTINENCE DEVICE, SYSTEMS AND METHOD

CROSS-REFERENCE TO RELATED APPLICATIONS

This application is a continuation of U.S. patent application Ser. No. 12/376,294, filed Feb. 4, 2009, which is a §371(c) entry from PCT/IL2008/01450, filed on Nov. 5, 2008, which claimed the benefit of U.S. Provisional Application Nos. 61/064,374 filed on Feb. 29, 2008, and 60/996,275, filed on Nov. 8, 2007, the full disclosures of which are incorporated herein by reference.

BACKGROUND OF THE INVENTION

The present invention relates to devices and methods suitable for treating fecal incontinence.

Fecal incontinence (also referred to as anal or rectal incontinence or accidental bowel leakage) is a disorder afflicting both children and adults with devastating social and psychological affects. It is estimated that in the United States alone more than 5.5 million individuals suffer from fecal incontinence and that the incidence rate of this disorder is 1-5%. Fecal incontinence is a major factor limiting the rehabilitation of the elderly and disabled, preventing many of them from being cared for at home. Mild to moderate incontinence accounts for about 80% of the market (gas, liquid and soiling) while severe incontinence accounts for the remaining 20%.

Fecal continence results from a coordinated motor function of anal sphincters and pelvic floor muscles, the role of the rectum and sigmoid colon as a fecal reservoir with capacitance and compliance and as a propulsive force with intrinsic motor activity, the effects of stool consistency, volume and delivery rate, the anorectal angle, and anorectal sensation.

The most common causes of fecal incontinence are structural or functional deficiencies of the sphincter muscles. Such deficiencies can result from anatomic disruption of the sphincter mechanism which may be caused by obstetric injuries (perineal laceration and improperly performed median episiotomies), complications of hemorrhoid, fistula or fissure surgery (keyhole deformities), traumatic injuries (e.g., impalement injuries), or cancer or from deterioration of the sphincter muscles due to age, congenital disorders, systemic and metabolic diseases, acquired neurological defects, and diseases of the colon and rectum.

Anal sphincters are muscular structures that assist in controlling the flow of feces and release of flatus from the colon. The internal anal sphincter (IAS) and the external anal sphincter (EAS) encircle the anal canal and form a part of the anorectal ring (see FIG. 1). The IAS is a thickening of the gastrointestinal smooth muscle; it maintains continence at rest. The EAS is composed of striated, voluntary muscle. The EAS, the puborectalis, and the levator ani muscles work in concert to prevent leakage of flatus and feces when there is an increase in abdominal pressure or when the internal anal sphincter relaxes after rectal distention.

Resting pressure in the anal canal is typically 60 mm Hg (1.1 psi), increasing up to 100 mm HG (1.9 psi) in strain or forced exertion. In a normal individual (normal parameters vary widely), the myogenic activity of the involuntary internal sphincter contributes about 10% of the anal resting pressure, and 45% is due to the sympathetic innervation of the internal sphincter, for a total of 55%. The remainder of the resting tone is from the hemorrhoidal plexus (15%) and the external anal sphincter (30%). The external sphincter supplies 100% of the voluntary short-term squeeze pressure.

Therefore, what is needed to improve continence is a technology that can influence the ability of the anus to seal better in the resting state while not interfering with the distention function of the sphincter during defecation.

Present treatment approaches for restoring fecal continence include non-surgical and surgical therapy. Non-surgical therapy for incontinence include biofeedback and perineal strengthening exercises beneficial in alleviating symptoms of seepage and occasional loss of control and electrical stimulation to improve contraction of the sphincter muscles.

Surgical therapy approaches include implantation of artificial valves (see, for example, U.S. Pat. Nos. 6,471,635, 6,749,556, and U.S. patent application Ser. Nos. 10/269,949 and 10/651,851), injection of bulking agents into the anal mucosa or the anal sphincters (see, for example, Vaizey and Kamm, British Journal of Surgery 2005; 92: 521-527), implanted electrodes for stimulating the pudendal or sacral nerves (see, for example, U.S. Pat. Nos. 6,907,293 and 7,054, 689) or sphincteric muscles (see, for example, PCT publication No. WO06047833).

Fecal incontinence can also be partially controlled using absorbent pads, absorbent plugs or hard plugs/valves and the like, however, such approaches are not well tolerated by individuals due to efficacy, convenience and comfort limitations as well as sealing limitations.

Thus, there remains a need for a device and method for treating fecal incontinence which are devoid of the above limitations.

BRIEF DESCRIPTION OF DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION

Figure 1:
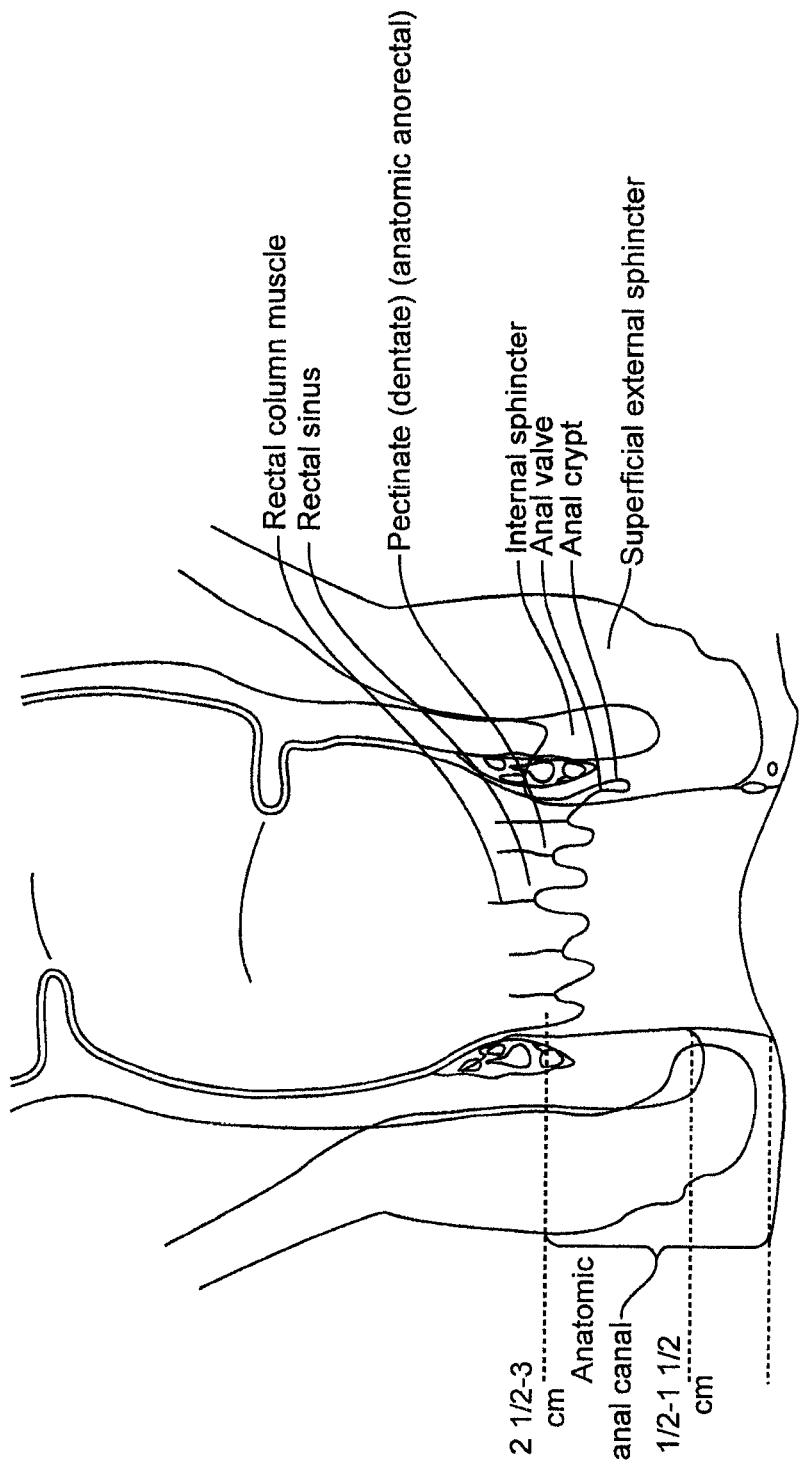
FIG. 1 is an illustration of the anatomy of the anal canal and associated tissues.

The present invention is of devices, systems and methods which can be used to treat incontinent passageways. Specifically, the present invention provides a novel passageway plugging approach which can be used to treat fecal incontinence.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Fecal incontinence is a socially devastating disorder which affects at least 2.2 percent of community dwelling adults and 45 percent of nursing home residents. People who have fecal incontinence may feel ashamed, embarrassed, or humiliated; some don't want to leave the house out of fear they might have an accident in public. Treatment of fecal incontinence depends on the cause and severity of the disorder.

Severe cases are typically treated by surgeries for repairing damaged sphincters, reinforcing anorectal structures, implanting artificial sphincters, and transferring muscle tissue. Mild to moderate cases of fecal incontinence are typically treated using special diets, medication, bowel training, or diapers. Although the latter approaches can reduce fecal discharge or help contain fecal discharge in some patients, they are either ineffective or are unacceptable for many patients.

Thus, despite the availability of pharmacological, behavioral and surgical treatments for fecal incontinence, many patients remain symptomatic.

To overcome the deficiencies of diapers and yet provide an easy non-surgical solution to this problem, use of anal plugs has been suggested. Such plugs are typically preformed from hard polymers or soft absorbent materials. The plug is introduced by the patient through the anal canal and into the rectum and much like a tampon is designed to contain or block any discharge.

Although such plugs have been proven somewhat effective in containing solid fecal discharges they are not efficient in containing liquid discharge and in addition are not well tolerated by patients (see, Deutekom and Dobben, "Plugs for containing faecal incontinence" 2007 The Cochrane Collaboration. Published by John Wiley & Sons, Ltd).

The present inventors have postulated that a plug devised for positioning mostly within the anal canal while being capable of maintaining the anal canal free of fecal solids or liquids would be advantageous over prior art rectal plugs since the anal canal is less sensitive than rectal tissues. In addition, in contrast to the teachings of the prior art, the present inventors further believe that due to the dynamic nature of the rectum walls opening up laterally during filling [McMahon et al. Neurogastroenterol. Motil. (2005) 17, 531-540], plugs that attempt to seal against the side walls of the rectum with sponge or balloon type plugs are prone to leakage as the rectum walls invariable pull away from the sealing surface as the rectum fills with fecal matter. To produce sufficient force on the rectal walls to enable sealing, prior art plugs have to be at least 30 mm in diameter and as a result, such plugs are difficult to pass, and are intolerable due to the pressure on the rectal walls being felt by the patient as an urge to evacuate. On the other hand, the plug of the present invention seals against the relatively stable geometry of the bottom neck portion of the rectum and/or the side walls of the anal canal, and as such exhibits superior sealing capabilities. Furthermore, physical pressure on the side rectal walls or occupying more than a few cubic centimeters in the rectum causes unpleasant sensations and a desire to defecate, whereas a plug made of soft material seated at the bottom region of the rectum and in the anal canal is essentially imperceptible. As an analogy, prior art plugs attempt to seal against the walls of the bathtub whereas the plug of the present invention seals downwards on the drain directly.

In order to design a plug capable of anchoring and sealing at the anal canal, the present inventors formed impressions of the anal canals and lower rectums of both continent and incontinent human subjects using an injectable vinyl polysiloxane (VPS) impression material. VPS material was introduced into the rectum and anal canal as a liquid and polymerized in situ into a plug that blocked the anal canal with a highly ridged and thin "stem" and formed a small "cap" in the lower rectum (see FIG. 2), effectively restoring continence to severely incontinent patients. The plugs were evacuated on their own along with fecal matter during the next voluntary bowel movement. Observations made on evacuated plugs led the present inventors to notice that upon defecation, fecal matter was impacted along the top and side surface of the cap, but no fecal matter touched the lower neck surface of the cap or the stem that was present in the anal canal. These unexpected findings indicated that the sealing occurs not against the lateral rectal walls, but rather along the bottom portion of the rectal neck where it transitions into the anal canal, and in the anal canal itself.

The shapes of the expelled plugs demonstrated that anal canal walls are highly folded (FIGS. 2 and 6A) thus suggesting that a plug design capable of effectively anchoring and sealing in the anal canal must conform to the anatomy of the canal walls. The VPS plug molded itself perfectly within the complex and unique geometry of each patient's anal canal and rectum and could not be felt by patients due to the fact that it did not stretch or deform the rectum or anal canal. Unexpectedly, there were just a few differences in the macroscopic shapes of the expelled VPS plugs between continent and incontinent patients. VPS plug 20 in FIG. 3 was formed in a normal subject whereas VPS plug 30 in FIG. 3 was formed in a severely incontinent subject. All plugs showed an approximately 60 degree widening of the neck of the lower rectum with an elliptical cross section as viewed in a transverse section of the cap that fits within a rectangle of approximately 20 mm.times.10 mm at a height of approximately 15 mm above the top of the anal canal. As seen in FIG. 3, the key differences in the plugs between normal subjects and those suffering from fecal incontinence are: [0035] i. The stem regions of VPS plugs right below the cap portion of subjects with fecal incontinence had greater cross sectional area (approximately 10-40 mm.sup.2) than the stem region of normal subjects (approximately 1-2 mm.sup.2). This implies that there was less resting pressure in the anal canal to push away the liquid VPS before it polymerized. The polymerized VPS stem formed a perfectly anatomical internal mandrel against which the anal canal could seal even without significant resting pressure, and therefore the VPS plugs dramatically improved the continence of these FI subjects. In normal subjects, the area at the top of the VPS stem was paper thin, indicating the proper functioning of a high pressure zone in the anal canal where the primary sealing occurs. It is therefore hypothesized that a major design parameter of pre-formed plugs of the present invention that will allow for a limited range of pre-sized plugs to work for patients suffering from light to severe fecal incontinence will be the shape, size and mechanical properties of this part of the stem. [0036] ii. The angle of the rectum versus the anal canal is highly curved backwards in continent subjects and less so in incontinent subjects. [0037] iii. The length of the anal canal is somewhat longer in continent subjects than in incontinent subjects.

As is further described hereinunder, the present inventors generated several plug designs which incorporate features derived from the VPS plugs and are important for both sealing and anchoring the plug in the anal canal. While testing these plugs it was further uncovered that by using an ultra-soft and elastic form-fitting plug body, a single universal plug design in a few pre-set sizes can fit most if not all incontinent patients, including smaller sizes for pediatric patients.

Thus, according to one aspect of the present invention there is provided a plug useful in preventing unwanted discharge of fecal fluids or solids. Such a plug can be used by subjects suffering from incontinence caused by neural damage, muscle damage or both, or by subjects suffering from incontinence caused by an irritable bowel (e.g. inflammatory bowel disease, irritable bowel syndrome, ulcerative colitis, Crohns disease and the like).

The plug of the present invention is constructed capable of:
(i) residing primarily in the anal canal with a small top portion being in the lower rectum region and optionally a small bottom portion residing outside the rectum against external tissues and elastically connected to the top portion;
(ii) sized and shaped to fit the natural anatomy of the anal canal and/or the lower rectum;
(iii) being of sufficiently soft and elastic material or covered by or filled with a soft material such that it is essentially imperceptible and conforms to the anatomy of the anal canal and lower rectum, even during movement;
(iv) optionally include an invaginatable, flowable or moldable surface that conforms precisely to the surface morphology of the walls of the anal canal and lower rectum for improved sealing and anchoring; and
(v) being elastically stretchable in order to fit various anal canal lengths and to provide an elastic biasing force to help in anchoring and sealing Such features ensure that the plug effectively seals and anchors along the length of the anal canal and in the lower rectum thereby providing cooperative anchoring and sealing. In addition, the fact that plug conforms to the anatomy of the anal canal and lower rectum enables it to stay in place and seal without applying any perceptible pressure on the walls of the anal canal and/or rectum even as the rectum anatomy changes as the rectum fills with fecal matter.

Furthermore, since the plug body resides below the side walls of the rectum, it does not trigger sensory receptors present in rectal tissue and thus does not cause discomfort like prior art plugs as described above.

Figure 2:
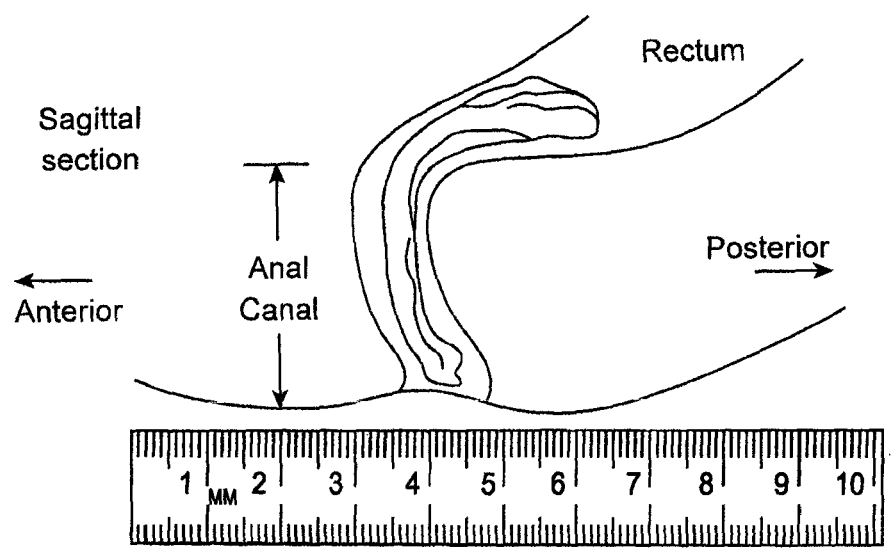
FIG. 2 illustrates the position of an in-situ formed vinyl polysiloxane (VPS) plug within an anal canal and rectum.
Figure 3:
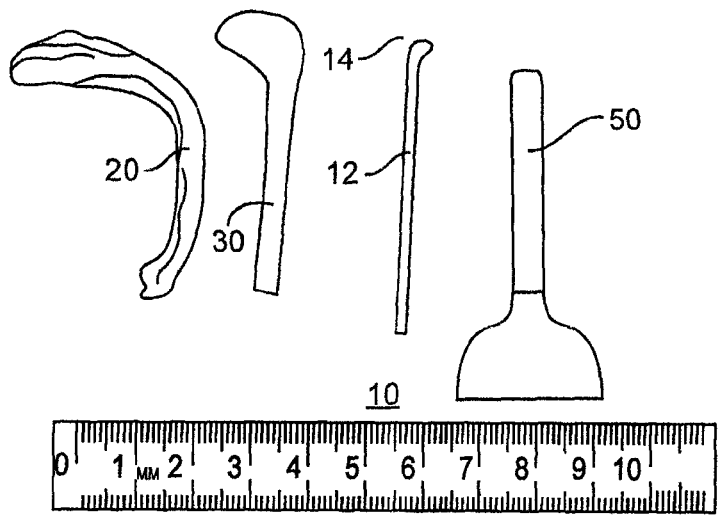
FIG. 3 illustrates a fecal incontinence plug and applicator constructed in accordance with the teachings of the preset invention compared with an image of in-situ fanned VPS plugs.

Thus, such a preformed plug would function similarly to the in-situ formed plug shown in FIG. 2.

FIG. 3 illustrates plugs 20 and 30 which are VPS impressions from a normal and a severely incontinent human subject respectively. FIG. 3 also shows one embodiment of the fecal incontinence plug of the present invention which is referred to herein as plug 10. Plug 10 is shown applied onto applicator 50 (which is further described hereinbelow).

Plug 10 of the present invention is designed such that it is capable of spanning the anal canal from the external anal orifice to the lower rectum. Sealing is primarily provided in the lower rectum and upper anal canal regions where the anal canal transitions through a narrow neck region into rectal tissue.

It is well known that once the anal canal is exposed to fecal matter that escapes downward from the rectum, a positive feedback is initiated that relaxes the internal anal sphincter and causes an uncontrolled and immediate urge to defecate. It is hypothesized that by preventing fecal matter from reaching the anal canal in the first place, the chemical and/or mechanical sensors that trigger the sphincters to relax and the reflex to defecate are not activated and therefore the involuntary urge to defecate is reduced in at least some of the incontinent patients. In this scenario, the body's natural sphincter mechanism and the plug's minimal sealing of the lower rectum and upper anal canal regions augment each other and work cooperatively to prevent leakage of fecal contents into the anal canal and hence restore continence. In contrast, prior art plugs don't augment the body's natural sealing mechanisms, but rather try to block the passage of fecal contents mainly with their bulk, size or absorption capabilities.

In order to accomplish the functionality described above, the fecal incontinence plug of the present invention is preferably characterized by several distinct features. It includes an elongated body (also referred to hereinbelow as stem portion 12) which at least some portion of which is preferably capable of elastically stretching to accommodate several lengths of anal canals (and thus fit different individuals) and also to allow overshoot of anchoring element (also referred to hereinbelow as cap portion 14) high into the rectum so that cap portion 14 which is introduced into the anal canal concave down due to drag forces during insertion seats in the lower rectum concave up during applicator 50 withdrawal.

With reference to FIGS. 6B-9, plug 10 includes at least one, preferably two protrusions, one at each end of the elongated body; the first protrusion (also referred to hereinbelow as anchoring element or cap portion 14) mainly functions in sealing while also providing some anchoring, whereas the second protrusion (also referred to hereinbelow as biasing cap or biasing element 21) functions in maintaining the plug within the anal canal (by providing a force countering upward movement of plug 10 in the neck portion of the rectum). The embodiments of the present plug described hereinbelow provide more detail as to specific plug portions and their function. It will be appreciated that although such embodiments are presently preferred, alternative plug configurations, including, for example, configurations having a diaphragm with an elastic rim or a hollow windsock or inverted conical condom shape with the open end in the lower rectum with a stiffening ring keeping the open end pressed against the lower rectum and the windsock body or condom sheath resting in the anal canal where the fecal contents themselves fill the windsock or sheath and form the plug are also envisaged herein. Such configurations can be implemented with or without biasing element 21 to keep the plug in place.

As is shown in FIG. 3, one embodiment of plug 10 includes a stem portion 12 which is attached to or contiguous (co-formed) with an anchoring portion (also referred to herein as cap portion 14); forming a structure similar to a golf tee or to the in-situ molded VPS plugs shown in FIGS. 2 and 3.

Figure 5A:
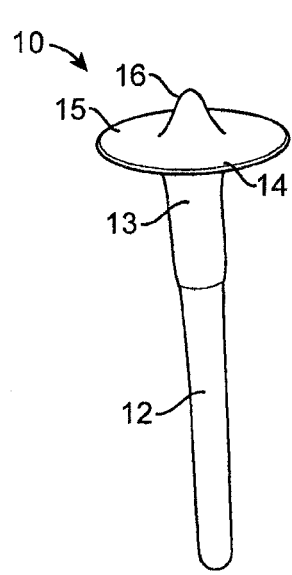
FIGS. 5A-C illustrate an alternative embodiment of a fecal incontinence plug and applicator constructed in accordance with the teachings of one embodiment of the present invention.

Stem portion 12 can be a substantially cylindrical rod with a length ranging from 0.5 to 6 cm and a diameter of 0.1 to 1 cm. The stem can be grooved, ridged, textured, or composed of stacked discs or many smaller parallel filaments (round or hexagonal tassel-like filaments that can rearrange dynamically to fill any shaped cross section) to increase surface area or to better conform to the natural folds in the anal canal. The ridges can be designed such that the mucosal surfaces form around them and therefore improve the seal of plug 10. As shown in FIG. 5A, at the top of stem portion 12, there can be a stem upper region 13 with different geometrical, physical, mechanical or chemical properties given that this is hypothesized to be a primary region of sealing that needs reinforcement in fecal incontinence patients. Stem upper region 13 is intended to sit in proximity to the primary sealing region of the anal canal, which is towards its top based on the experimental results of the present inventors with the VPS plugs. For example, stem upper region 13 can be a harder material, or a fluid, gel, gas or particle filled balloon that applies gentle pressure against the anal canal with dynamic geometry and uniform pressure distribution. Uniform pressure distribution is important in the anal canal as this region is in contact with the internal hemorrhoids which are pressure and abrasion sensitive.

Stem portion 12 can be fully in the anal canal with no part of it exposed, or can extend below the anal canal and a portion exposed between the patient's legs, allowing the patient to pull stem portion 12 and seat cap portion 14 against the lower rectum or remove plug 10 altogether from the rectum. Cap portion 14 is designed to apply pressure to the lower rectum in the direction of fecal flow. As such cap portion does not apply any substantial radial forces to the rectal walls; in fact the preferred configuration of cap portion 14 is a flat or bowl-shaped disc which is designed to seat on top of the lower rectum at the point where it narrows and transitions into the anal canal and act in a manner similar to a drain plug. As such, anchoring of cap portion 14 results from forces applied largely to a bottom surface of cap portion 14 and not on the periphery thereof.

Stem portion 12 can include within it or be comprised of a non-elastic drawstring that is over-molded by cap portion 14 and perhaps also parts of stem portion 12 itself. Preferably, at least some part of stem portion 12 is axially flimsy and radially elastic to enable it to conform the various and dynamic curvatures of the anal canal as explained more fully below.

Figure 6A:
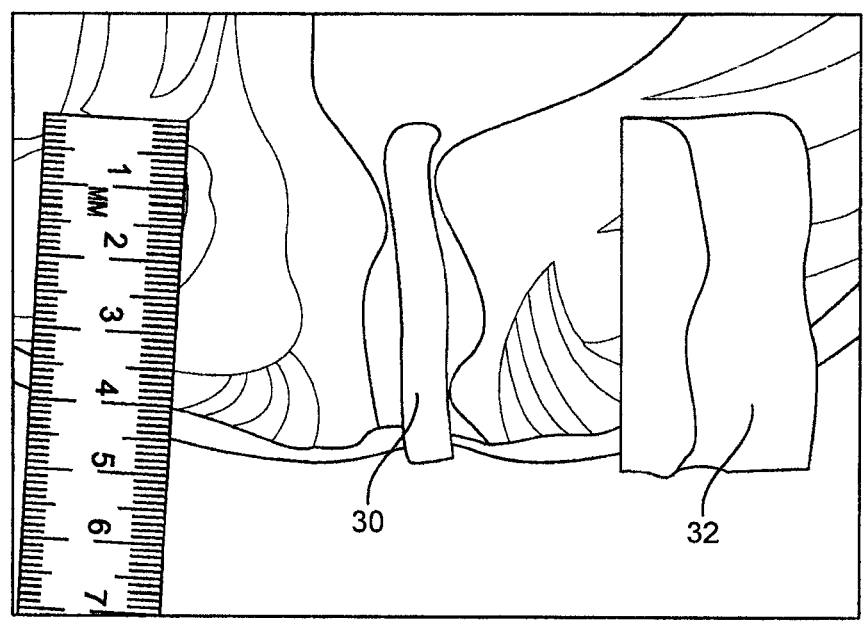
FIG. 6A illustrates an in-situ formed VPS plug superimposed over a sagittal plane view of the anal canal (left) and a negative mold of the in-situ need plug (right).
Figure 6B:
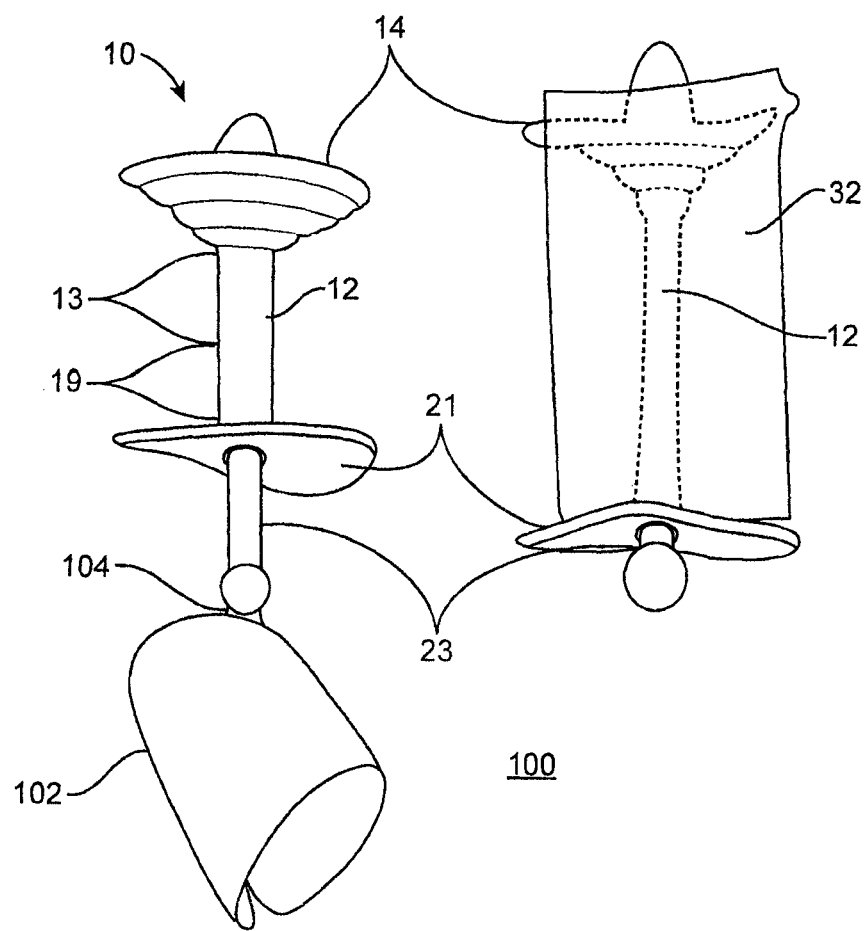
FIG. 6B illustrates one embodiment of the fecal incontinence system of the present invention (left) along with the positioning and fit of the plug in cross section within the anal canal as is demonstrated via use of a molded model of the anal canal from an incontinent patient (right).
Figure 7:
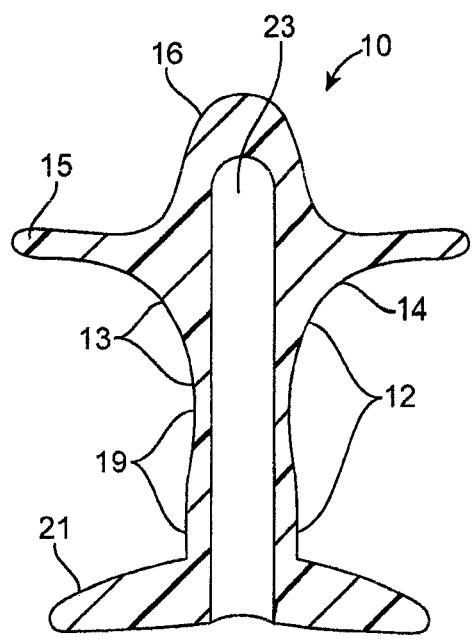
FIG. 7 is a cross sectional view showing specific features of the plug of the present invention.

Stem portion 12 can also include a biasing element 21 (also referred to herein as biasing cap 21) attached opposite cap portion 14 (see FIGS. 6B and 7 for example). FIG. 6A shows VPS plug 30 superimposed against an illustration of the anal anatomy, along with negative mold 32 of VPS plug 30 which represents the actual rectal and anal anatomy of the patient. On the right side of FIG. 6B, a cut-away plug 10 is inserted into negative mold 32 to demonstrate the fit of plug 10 into the natural geometry of the lower rectum and anal canal. Biasing cap 21 functions in securing plug 10 within the anal canal and preventing plug 10 from riding up into the rectum due to displacement by fecal matter or due to contractions of the rectum against a wedge-shaped cap portion 14 which generates an upward force. As such, when plug is positioned within the anal canal (using the steps shown in FIGS. 8A-C) and cap portion 14 anchored in the lower rectum, biasing cap 21, which resides outside the anal canal (against the skin external to and surrounding the anus, see FIG. 6B) applies a gentle pulling force on stem portion 12 thereby causing slight stretching and adjustment of the length of stem portion 12 to correspond to the length of the anal canal. Following positioning, biasing cap 21 resides against the external surface of the anus effectively providing a counter force of 100 grams or less to the anchoring of cap portion 14. Such a biasing force is distributed over a few square centimeters of soft material of biasing cap 21 and hence is a very gentle and effectively imperceptible counter force which can be tolerated for many hours or even days without discomfort as demonstrated in the examples below.

As the anal canal does not like to be occupied and tends to push out any foreign objects within it, plug 10 would tend to be pushed up into the rectum without biasing cap 21 therefore compromising the seal of cap portion 14 against the lower rectum. Likewise, plug 10 would tend to be pushed outward and out of the body and end up between the patient's legs without the anchoring of cap portion 14. The balance of forces between cap portion 14 and biasing cap 21 through an elastic element allows for stable and self-contained positioning of plug 10 in the anal canal at all times, without the need for user adjustment or intervention, external tubes, tape, string or other anchoring schemes which may cause discomfort.

Cap portion 14 and biasing cap 21 can each be independently shaped as, for example, an inverted cone with the tip contiguous with stem portion 12, as a diamond-profiled head with conical surfaces on the top and bottom, as a spherical or conical balloon (which can be fully or partially filled with fluid, gas, particles or a gel), a skirted balloon or a balloon connected to a disk, bowl or rim element that deforms to seal the lower rectum, a ring, or as a cupped or flat disc or set of disks with a circular or elliptical transverse cross section. Cap portion 14 can also be a random collection of squishy "tentacle-like" filaments that collapse together to form a physical obstruction to the passage of fecal matter through the anal canal. As shown in FIG. 5A, cap portion 14 can have a fixed, detachable or dissolvable nose cone 16 on top to facilitate easier entry into the anal canal.

In the preferred configuration, cap portion 14 is a flexible flat disc. Such a configuration minimizes radial contact between cap portion 14 and the rectal walls and enables cap portion to conform to the subjects anatomy and provide an efficient and adaptable seal.

As shown in FIG. 5A, cap portion 14 or a portion thereof can be a disk 15 with thickness of 10-3000 microns, with or without stiffening and shaping rings, ridges or ribs. Disk 15 can be elastically folded forward and retained in this position to form nose cone 16 and then released when in the rectum to create a barrier element. If unrestrained, disk 15 folds backwards into the anal canal during insertion and upon withdrawal of the applicator, disk 15 folds forward and seats in the lower rectum to provide additional sealing and anchoring capabilities to plug 10. Cap portion 14 can take the form of an inverted umbrella biased open by its natural relaxed state, elastic ribs or via a mechanism activated through the applicator. Cap portion 14 can be made of two or more elements, for example as a balloon for anchoring and flat or pleated skirt for sealing or a series of discs of variable diameter arranged one on top of the other (see FIG. 6B for example). The diameter of cap portion 14 can range between 0.5 to 5 cm. Cap portion 14 can have sufficient size and rigidity so as to not migrate downward into the anal canal, but still be small enough to not be felt and to be evacuated easily. The less mass there is in the upper cap portion 14, the less likely it is that the rectum will have something to push against when trying to void plug 10 out of the body. A cross sectional area in the range of 0.5-5 sq cm should be sufficient for anchoring yet not be felt nor be so bulky as to provide mass against which the rectum can push to void it until a full defecation is underway. The overall volume of plug 10 can range between 0.5 to 10 ml, preferably 1-3 ml.

Plug 10 can be constructed as a hollow or solid structure or a combination of hollow and solid portions. For example, stem portion 12 can be constructed as a hollow or solid rod while cap portion 14 can be fabricated as a solid cone or disc or as a hollow sphere or vice versa. Any hollow spaces can be filled with a internal sleeve, liquid, gel, gas, foam or solid particles.

Biasing cap 21 is constructed so as to provide external anchoring which maintains a slight pulling force on cap portion 14. In addition, since biasing cap 21 resides outside the anus and against external tissues of the subject, it should be configured for maintaining tissue contact while providing the necessary (although minimal) restraining force on cap portion 14 and enough surface area such that it is not pulled into the anal canal and distributes the restraining force over sufficient tissue area to prevent discomfort (for example a downward-facing bowl-shaped disk .about.2.5 cm in diameter, 1 mm thick, made of shore A 3 silicone). Thus, biasing cap 21 can be fabricated from soft thin material as a flat, yet foldable sheet which can be, for example, disc-shaped. A preferred configuration of cap portion 14 and biasing cap 21 is shown in FIG. 7. Since biasing cap counters an anchoring force applied by cap portion 14, it does not need to be attached via adhesive or other means to external tissues of the subject in order to maintain plug 10 in position, but merely needs to be in biasing contact with external tissue (e.g. tissue surrounding external surface of anal orifice.

Plug 10 does not need to appreciably change in volume, girth or shape following introduction thereof into the anal canal in order to facilitate anchoring and/or sealing.

Thus, anchoring of plug 10 within the anal canal and rectum does not require uptake of fluids by portions thereof residing within the anal canal/rectum (i.e. cap portion and stem) and does not require activation or any shape change (e.g. as facilitated via inflation). As such, plug 10 can be constructed from non-porous, non-absorbent material which is not structurally modified following insertion. This is in contrast to prior art plugs which typically anchor within the rectum via a 2-3 fold expansion in volume (via fluid uptake, relaxation of compressed shape, or inflation). This feature of plug 10 of the present invention ensures that it does not exert any appreciable radial pressure on the walls of the rectum or anal canal and as such does not cause sensation or discomfort when in use. Since plug 10 does not exert any significant forces on the tissue lining the anal canal and rectum it can be utilized over extended time periods (days). Prior art devices such as the ProCon 2 are typically limited to 8 hour use periods since extended use can lead to capillary blood flow blocking and tissue necrosis.

Furthermore, the small size of Plug 10 ensures that it can be evacuated naturally without user intervention or discomfort as is it smaller in diameter than feces, whereas the prior art plugs need to be deflated or pulled out at a size larger than the relaxed anal canal, causing significant discomfort and inconvenience. Plug 10 is configured so that it in its sealing-capable configuration (i.e. no further change of volume needs to occur to effect sealing) plug 10 can be elastically deformed to enable easy entry and exit through an opening 2.5 cm in diameter or smaller.

As is mentioned hereinabove, plug 10 relies on anchoring at the stem and/or cap portions. When anchored at both the stem and cap portions, cooperative anchoring is achieved by the combination of two separate anchoring mechanisms, a downward force biasing cap portion 14 against the neck-like structure above the anal canal and an adherence/frictional force between stem portion 12 (and optionally cap portion 14) and the surface of the anal canal wall in which stem portion 12 resides. Additionally, cap portion 14 can be designed that fecal matter and liquids accumulating on top of cap portion 14 serve to better anchor plug 10 in place by applying a downward force thereupon, and therefore also improve the seal against the lower rectum. This is in contrast to prior art plugs that seal against the sides of the rectum. Since with such plugs the filling of the rectum by fecal matter moves the tissue away from the sealing surface and weakens the sealing and anchoring by allowing fecal matter to flow around the prior art plug thus allowing fecal matter to enter the top of the anal canal and cause an urge to defecate.

The anchoring schemes described herein ensure that plug 10 remains secured in place and enables compensation for temporary loss of anchoring (e.g. during anal canal movement). Human subjects that have used both the VPS plugs and plug 10 of the current invention report no problem in passing gas around the plug. Neither the VPS plug nor plug 10 of the current invention are permeable to gas. Therefore, it gas escapes around plug 10 by temporarily detaching a region of cap portion 14 from the tissue, but since plug 10 is also anchored at stem portion 12 and at other regions of cap portion 14, such escaped gas will simply travel as a wave along the outside surface of plug 10 and not completely dislodge plug 10 from its position.

In a further embodiment of the present invention, gas release channels or valves can be built in to plug 10 to enable gas to pass through plug 10, to further facilitate passing of gas. Such channel can open under preset pressure differentials, and be open channels or protected with gas-permeable/water-impermeable filters such as hydrophobic foams. The inner lumen of stem portion 12 can form such a conduit or channel.

An additional advantage to the anchoring scheme of the present invention is the ease of evacuation the plug upon defecation. Most prior art plugs require a removal mechanism (e.g. deflation of a balloon or pulling on a draw string) in order to facilitate removal of the plug. As is mentioned above, such a mechanism is necessary in prior art plugs since their rectal positioning and anchoring scheme (via radial expansion) implies that they are substantially larger than a relaxed anal canal (3-6 cm diameter) and thus are difficult to pass.

Since plug 10 of the present invention does not rely on a radial force or a large diameter anchor for anchoring, the act of voluntary defecation naturally dilates the anal canal, thereby detaching the top anchoring of plug 10 and enabling effortless evacuation thereof along with the fecal matter. It has been demonstrated in incontinent patients with the VPS plugs described herein as well as patients with plug 10 that even in cases where there was no voluntary control of defecation due to severe neurological deficits, the use of a plug of which is similar in size and shape to the plug of the present invention prevented continuous leakage of fecal contents, thereby allowing sufficient fecal matter to accumulate in the rectum to restore the natural feedback to have regular bowel movements. The use of plug 10 of the present invention enabled these patients to defecate on a regular schedule with no leakage in between bowel movements, thereby restoring control of their defecation behavior.

Cap portion 14 is preferably configured to facilitate insertion into the anal canal, it may also be coated with a lubricant on its upper surface. Such a lubricant can be present in grooves, ridges or dimples on the top portion of cap portion 14, or applied thereto just before use and restrained from dripping off plug 10 by the surface features above, or by a circumferential dam. The packaging protecting plug 10 can also have a form-fitting inner face that retains a layer of the lubricant on the top portion of cap portion 14. Alternatively, a peel off protective layer can protect the lubricant and be removed by the user just prior to use. Appropriate personal lubricants are well known in the art, being pre-applied to enema tips for example.

Stem portion 12 can include an insert for stiffening stem portion. Such an insert (23 in FIGS. 6B and 7) can be used to stiffen stem portion 12 thus facilitating insertion of plug 10, as well as acting as a protective sheath for an in-plug applicator (further described hereinbelow with respect to applicator designs) thereby minimizing the chances that such an applicator perforates stem portion 12 or cap portion 14. Insert 23 can be longer than stem portion 12 (see FIG. 6B) and therefore extend outside the anus and serve as a handle and drawstring for manual removal of plug 10 if desired by the patient, or it can be shorter (see FIG. 7) and serve only to protect the plug from applicator puncture or stiffen stem portion 12 to improve the seal in the high pressure zone of the anal canal.

Insert 23 can also be used to facilitate an applicator-free positioning as is further described hereinbelow.

Experiments conducted by the present inventors have determined that a plug of the geometry in FIG. 7 was slightly uncomfortable when made of silicone of Shore A 40 or harder, but essentially unnoticeable when made of a silicone of Shore A 3. Therefore, in order to be comfortable and hence usable, plug 10 is constructed having minimal surface hardness required to maintain its basic shape and maximal compliance to surface and tissue anatomy. Such properties can be achieved by fabricating solid structures from soft materials such as low Shore silicone (e.g. <40 Shore A value), silicone-latex, open or closed cell foams (e.g. silicone or polyurethane) or by constructing plug 10 as a partially or fully fluid, gel or gas-filled hollow structure. Partial filling allows for the plug surface to fold and/or invaginate and better conform to mucosal folds. Preferably, plug 10 is also elastic such that it conforms to the shape of the anal canal during movement thus being effective in sealing while being compliant to tissue movement over extended time periods (hours to days). Plug 10 can also be constructed from a rigid yet partially elastic material which is coated with a soft material such as Shore A 3 silicone or constructed from a thin higher shore material filled with a gas, liquid, gel or comprised of a foam structure which lowers the effective shore of the entire structure to a comfortable level.

Stem portion 12 is preferably elastic and flimsy so as to enable fitting of plug 10 to individuals of varying anal canal lengths. Such elasticity ensures that plug 10 can be stretched and bent to accommodate anal canals of varying lengths and geometry. Preferably, stem portion 12 is fabricated with variable elasticity along its length such that a lower region of stem portion 12 stretches more than an upper region (adjacent to cap portion 14) when plug 10 is fitted.

For example, stem portion 12 can be fabricated such that a lower region thereof is elastic and thus stretchable while an upper region is less elastic (or even rigid) and thus less stretchable. Such a configuration ensures that plug 10 can accommodate various anal canal lengths by stretching at a lower region thereof and not an upper region. Enabling plug 10 length accommodation without stretching or distorting an upper region of stem portion 12 as well as cap portion 14 attached thereto, ensures that the sealing function of stem upper region 13 against the high pressure zone of the anal canal and cap portion 14 are maintained.

An example of a stem portion 12 having such variable elasticity is shown in FIG. 6B. In this configuration, an internal sleeve 23 which runs the length of stem portion 12 is attached to upper region 13 and not lower region 19 of stem portion 12. Thus, stem portion 12 is capable of appreciably stretching at lower region 19 and the configuration of upper region 13 and cap portion 14 are maintained and their sealing functions remain unchanged regardless of the length of anal canal to which plug 10 is fitted.

Anal canal length ranges from about 2-5 cm (Morren G. L., British Journal of Surgery, 2001, 88, 1506-1512 and Gold, D. M., British Journal of Surgery, 1999, 86, 365-370). Thus, lower region 19 is configured to elastically stretch so as to accommodate such variance in canal length without affecting the diameter and shape of upper region 13 and cap portion 14. Any friction between lower region 19 and internal sleeve 23 or the inner sleeve and the applicator can be reduced via use of various lubricants (e.g. talc, paraffin, glycerin, PEG, mineral oil and the like).

FIG. 7 is a cut-away cross-section of one configuration of the plug of the present invention. This Figure illustrates nose cone 16 which facilitates delivery, soft upper disk 15 of cap portion 14 which is configured for sealing at bottom of rectum, and the cylindrical seal of the upper region 13 which rests against the anal canal high pressure zone of stem portion 12. Also illustrated is the thin highly-elastic lower region 19 of stem portion 12 that stretches to accommodate variable lengths of anal canals and allows overshoot upon plug insertion. Lower region 19 of stem portion 12 is 0.4 mm thick and has a cross sectional surface area of around 1 sq mm to enable high elasticity and deformations with low forces. Biasing cap 21 rests outside the anus to retain plug 10 in position, while insert 23 is made of harder silicone and provides more stiffness to upper region 13 of stem portion 12 in order to prevent applicator perforation of plug 10.

Plug 10, or portions/layers thereof, can be made of a hydrophobic material, in which case an open-cell foam will allow for gas to vent through the plug without the passage of liquid or solid fecal matter, or a hydrophilic material, in which case a closed cell foam would be preferable. In general, a hydrophobic material is preferable to minimize seepage of liquid between the tissue and plug surface.

In a further embodiment, plug 10 or portions thereof are made of a biodegradable material that can be flushed down the toilet and degrade naturally in the waste water. Such water degradation properties can occur over weeks or months, but not affect the ability of Plug 10 to function and withstand the humid environment of the rectum for hours or even days. Example materials include collagen, gelatin, gum, agarose, hydrogels, materials used in denture adhesive, or the like.

Dissolution of the biodegradable material comprising plug 10 or portions thereof can proceed from the surface. The dissolved polymers can form a tight seal by fitting within the smallest of mucosal folds, as long as the viscosity of the dissolved polymer is sufficiently high and lubrication is controlled. Other biodegradable materials include derivatized cellulosics, for example hydroxy methyl cellulose or polyvinyl alcohol. Such materials can be formulated in a hydrogel, hydrated and cross-linked or alternatively in a non-hydrogel, desiccated or non-crosslinked state (with appropriate moisture control packaging). Additionally, biodegradable or hydrolysable polymers can be made to have slow degradation times and generally degrade by bulk hydrolytic mechanisms. Such materials include as polylactic or glycol acids. Typical degradation times would be in weeks, over which time such material would lose its mechanical properties. Other degradable materials include certain polycarbonates or polyanhydrides, polymers and copolymers of phthalic acid, isophthalic acid with compounds like caprolactone or valerolactone, maleic anhydride or phthalic anhydride and the like. All materials listed above can be made in a soft formulation. Plug 10 can be made of combinations of biodegradable materials. For example inner sleeve 23 can be a hard plastic such as polylactic acid (PLA) encased in a softer gelatin or cellulosic outer plug.

Plug 10 or portions thereof can be fabricated by a compound that softens, plasticizes or even molds itself under humid conditions, at body temperature or under other conditions present or caused during plug 10 insertion, thereby increasing compliance to the natural tissue anatomy.

Plug 10 or portions thereof can be made of a solid core with a gel, liquid or gas filled blistered surface that allows for adequate surface conformation/invagination with the solid core provides structural rigidity.

Plug 10 can also be coated with a gel or gelling material (e.g. desiccated hydrogel). Such coating can provide additional surface impressibility (conformity to surface anatomy, e.g. folds of anal canal wall), better sealing and adhesion for improved anchoring and resistance to plug migration.

Plug 10 can also be filled with gel or fluid that exudes out of pores of the plug body to improve sealing.

Plug 10 can also be fabricated from an inelastic core which is overmolded with elastic soft material. For example, hydrated or dehydrated gelatin, agarose or other deformable, elastic or moldable polymer or hydrogel can be overmolded on an axially inelastic backbone, such as a string or collapsible tube (with insert).

For example, plug 10 can be dry coated with a layer of desiccated carboxymethyl cellulose which upon contact with anal and/or rectal tissue hydrates into a gel layer which follows the microscopic and macroscopic contours of the tissue folds. It will be appreciated that plug 10 coated with a hydrogel can be fabricated from a higher shore material since such a coating can provide the necessary compliance with tissue surface morphology.

Plug 10 or portions thereof can be coated with a high viscosity hydrophobic agent that might soften but does not flow at body temperature, such as various forms of grease or wax, to help prevent leakage of liquid fecal matter.

As is mentioned above, cap portion 14 is designed to seal at the rectal neck region at the top of the anal canal. Since the rectum is angled back with respect to the anal canal (see FIG. 2), plug 10 design must take into consideration this angulation and the effect of rectal tissue movement (e.g. radial expansion and forward distension of the rectum wall during rectal filling with fecal matter) on cap portion 14. Furthermore, this angulation changes from patient to patient and changes dynamically during the filling of the rectum for any given patient.

As is known in the art and as is evident by the shape of the VPS plugs used in the experiments underlying the present invention, the rearward angulation of the anal canal for patients with fecal incontinence is less than in normal patients. Restoration of this angle is normally accomplished only through surgical repair. In a further embodiment, plug 10 can be pre-curved and act as a semi-rigid internal armature that restores the appropriate puborectalis angle that will help restore a patient's continence. This effect can be in addition to or instead of the sealing effect of plug 10.

During rectal filling, the rectal canal widens to accommodate fecal matter. Such widening displaces opposing rectal walls and alters angulation between the anal canal and the rectum. In addition, fecal matter entering the rectum pushes down on the top of the anal canal region. A cap portion 14 which is not well seated in this region or contacts the walls of the rectum will be pushed aside (peeled') by the fecal matter. In such cases, a seal created by cap portion 14 can be compromised by the pressure of fecal solids and liquids migrating around cap portion 14 and into the anal canal. In order to prevent such displacement, cap portion 14 is designed so as to deform elastically to conform to the change of rectum geometry or to occupy a minimal footprint across the tissue above the anal canal ensuring that pressure from fecal matter along the walls does not displace it from its position or leak around the plug and into the anal canal. However, too small or soft of a cap portion 14 will allow migration of plug 10 down into the anal canal and the premature loss of plug 10. Lessons learned from the in-situ formed VPS plug of FIG. 2 suggest that the region above the anal canal can be effectively sealed by using a cap structure approximately 1-5 cm in diameter and that a cap having a low profile (e.g. flat disc, inverted cone) would not be displaced by feces. It will be appreciated that although the stem-cap configurations described above is presently preferred, configurations in which the stem portion is considerably shorter (e.g. 0.5-2 cm) or configurations which only include the stem portion or the cap portions separately are also envisaged. In a further embodiment, the cap portion can be connected to a fine elastic stem which itself is anchored to a biasing cap element that remains outside the anal canal between the legs of the subject. The very small diameter stem, shaped like a rubber band or elastic string, acts as an elastic tether between the cap portion and the external biasing cap thereby applying a predetermined force on the cap portion against the neck region of the lower rectum.

Plug 10 of the present invention, if made with an open top portion 14, can be used for stool sample collection. Fecal matter will be impacted into hollow stem portion 12, and then removed by pulling on biasing element 21 and sent for analysis without the patient needing to touch any fecal matter.

Plug 10 of the present invention can also be used to provide electrical stimulation to anal canal and rectal tissues. A plug 10 provided with electrodes and a power supply as well as circuitry and a controller can be used to deliver controllable electrical pulses to the wall of the anal canal and/or lower rectum for the purpose of stimulating, contracting and/or biofeedback training sphincter muscles surrounding these tissues. Power to plug 10 can be provided in the form of a battery or capacitor positioned within the plug or a coil which is positioned within the plug and activated via remote induction. A controller, which can either be positioned within the plug or within a remote device can be used to provide commands according to sensor data (from sensor positioned on the plug or elsewhere). Such stimulation to cause sphincter contraction, for example, can be activated only when a sensor senses fecal material in the rectum and/or a loosening of the anal sphincters.

Plug 10 of the present invention is preferably delivered using a dedicated applicator. FIGS. 4A-C and 8A-C illustrate delivery of plug 10 using such an applicator which is referred to herein as applicator 50 or applicator 100.

Figure 4A:
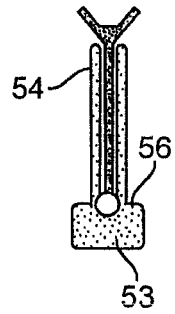
FIGS. 4A-C illustrate delivery and positioning of the fecal incontinence plug of the present invention.
Figure 4B:
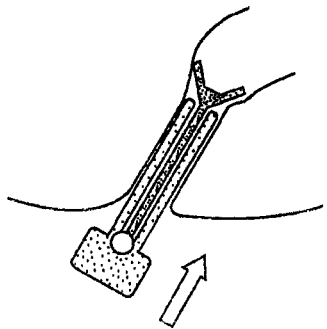
Figure 4C:
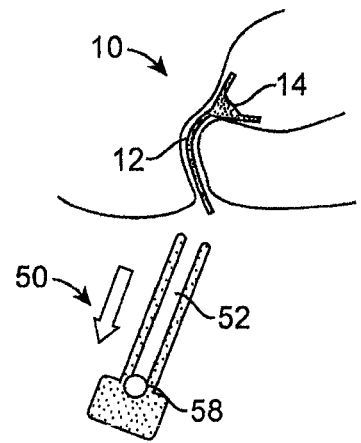

In the embodiment shown in FIG. 4A-C, applicator 50 is designed as a hollow tube and is sized for insertion into the anal canal.

Figure 5B:
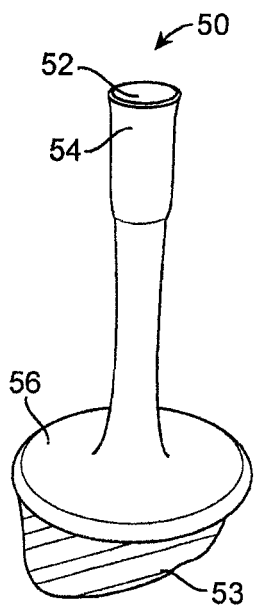
Figure 5C:
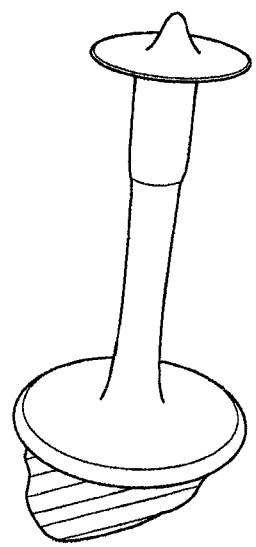

Plug 10 is pre-loaded into a bore 52 of applicator 50 with cap portion 14 protruding from applicator tip 54 (FIG. 4A and FIG. 5C). Upon insertion into the anal canal, cap portion 14 (shaped as a conical, cup-shaped structure in this example) is either inserted as is and deformed due to its softness, folded forward in applicator 50 or folded back against the outside surface of applicator 50. To this end, the surface of cap portion 14 can be pre-coated with a lubricant (e.g. aloe vera, paraffin, Vaseline™, Astroglide™ or KY™ gel) in order to facilitate insertion into the anal canal. Alternatively, cap portion 14 can be folded forward and held in place with film that dissolves in liquid to avoid the need to overshoot the lower rectum during introduction of plug 10. Applicator 50 is pushed with handle 53 (FIG. 5B) into a depth determined by a stop 56 at the base of applicator 50 such that it spans the anal canal with applicator tip 54 residing within the rectum and cap portion 14 assuming the position shown in FIG. 4B above the top edge of the anal canal. Applicator 50 is optionally fabricated as an elastic structure so it can follow the angulation of the anal canal-rectum passageway or it can be curved to allow for better conformance to the curved anal canal during insertion.

Once in position, applicator 50 is pulled back such that cap portion 14 contacts the narrowed neck region above the anal canal; the force of the neck region on cap portion 14 releases stem portion 12 of plug 10 from applicator 50, thereby positioning plug 10 following removal of applicator 50 (FIG. 4C). In order to ensure that plug 10 does not release from applicator prematurely or that it does not release if not in the correct position, bore 52 of applicator 50 can include a mechanism 58 which engages stem portion 12 of plug 10 and does not allow release until plug 10 is correctly positioned. Such a mechanism can be hand actuated or it can respond to a predetermined pulling force below which release does not occur. Applicator 50 can have a concave bowl-shaped forward tip to better support and directionally-stabilize cap portion 14 during entry into the anal canal. FIGS. 5A-C illustrates one preferred plug and applicator design.

An applicator can also be configured as an internal applicator which can fit within a hollow stem portion 12, or run alongside stem portion 12.

The left side of FIG. 6B illustrates a system which includes plug 10 fitted with an internal sleeve 23 and an internal applicator 100 which is designed to engage an internal bore of internal sleeve 23.

This configuration of applicator 100 includes a finger hold 102 which is designed to be fitted over a fingertip (e.g. index finger) and a rod 104 which is attached to finger hold 102 and is designed for fitting within sleeve 23 of plug 10 (FIGS. 6A-B). In that respect, rod 104 can be any shape and dimension suitable for insertion into sleeve 23. Preferably rod 104 is cylindrical in shape and is either hollow or solid in construction. Rod 104 is typically 1-10 cm in length and 0.1-5 mm in diameter. Applicator 100 can be constructed from a polymer such as polypropylene, polycarbonate, acetal, polybutylene terephtalate, polylactic acid or similar using known molding techniques and be either disposable or reusable.

Finger hold 102 of applicator 100 can be designed to accommodate any finger size by providing an adjustment (spring-loaded) tab within the finger-engaging portion. The diameter of the index finger first joint ranges between 1.5-2.3 cm for most individuals and thus a single design can be used to accommodate such a finger size range. An index finger application is preferred since this finger is the most developed with respect to kinesthetic feedback (proprioception), and thus most everyone can use this finger to guide plug 10 to the anal orifice.

As is mentioned hereinabove, sleeve 23 serves two functions, to prevent rod 104 from puncturing through plug 10 (and potentially damaging anal mucosa or rectal tissue) and to provide upper region 13 of stem portion 12 with the rigidity necessary to maintain its configuration even when plug 10 is stretched to accommodate anal canals of varying lengths.

Figure 8C:
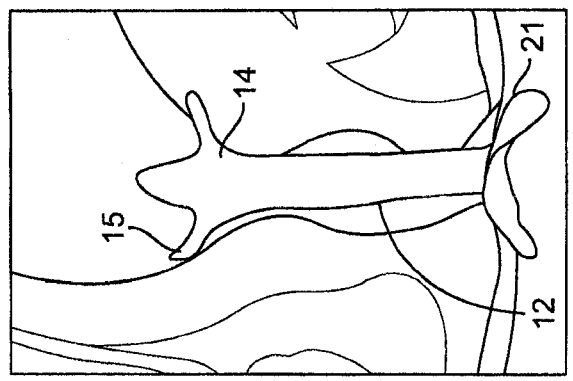
FIGS. 8A-C illustrate steps in administering the fecal incontinence plug of the present invention using a finger-operated applicator superimposed on an illustration of an anal canal showing plug positioning during each step of the administration procedure.
Figure 8B:
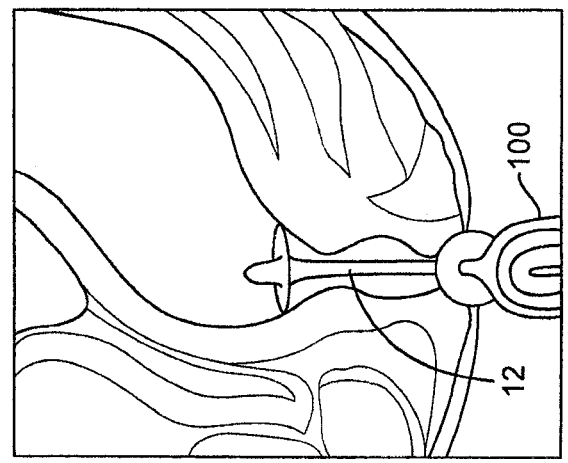
Figure 8A:
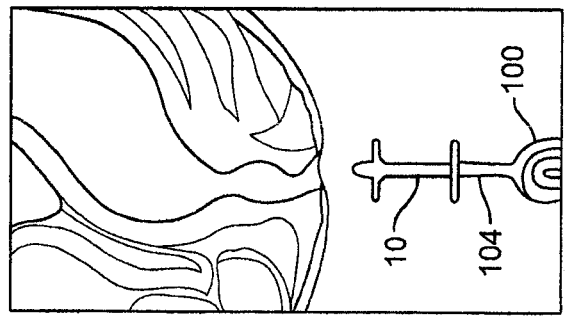

FIG. 8A-C illustrates plug 10 administration using applicator 100. In FIG. 8A, plug 10 is positioned over an illustration of the anal canal to indicate plug position with respect to the canal at every stage of insertion. Plug 10 is mounted on rod 104 of applicator 100. Due to its flimsiness, cap portion 14 folds backwards axially to reduce the cross sectional area of cap portion 14 during insertion in the anal canal. Lubrication of the top surface of cap portion 14 can be used to ease insertion. As shown in FIG. 8B, finger hold 12 is maneuvered to the entrance to the anus, thereby stretching stem portion 12 so that it touches finger hold 102. Disk 15 is lifted above the lower surface of the rectum. As shown in FIG. 8C, when applicator 100 is removed, disk 15 and stem portion 12 can return to their original shape due to inherent elasticity or some other shape-retention mechanism. The inner surface of internal sleeve 23 of plug 10 and applicator 100 and/or portions thereof can also be pre-lubricated for easier removal of applicator 100 following insertion of plug 10. Suitable lubricants include glycerin, polyethylene glycol, mineral oil and the like. A detent that provides a known friction against a ball feature at the tip of rod 104 can be provided within internal sleeve 23 in order to prevent plug 10 from falling off applicator 100 when held upside down. Such a detent can be configured such that the force applied thereby is low enough to still release when applicator 100 is removed following insertion of plug 10 into the anus. Experiments conducted by the inventors indicate that a retentive force of between 5 to 30 grams is ideal. It will be appreciated that following removal of applicator 100 from plug, the bare applicator rod may be harmful if reused to position the plug. Thus, to prevent reuse of applicator 100, the rod portion thereof can be fabricated from two or more lengthwise sections that split (curl out) once removed from stem portion 12. By splitting the rod of applicator 100 into smaller and sideward projecting rods, reuse is prevented. Alternatively, sleeve 23 can have within it a spring loaded tab that allows for applicator rod 104 to slide out but not re-enter internal sleeve 23, thereby also preventing reuse of plug 10. Another alternative configuration can also include a rod 104 that is pivotally attached at a base portion thereof to finger hold 102 and a sleeve 23 (of plug 10) which includes a lock ring at a lower portion thereof. The lock ring locks the pivot when plug 10 is positioned over rod 104 thus providing rod 104 with the rigidity necessary to allow plug insertion. However, when applicator 100 is removed from plug 10, rod 104 is no longer stabilized by the lock ring of sleeve 23 and thus it lacks the rigidity necessary for reinsertion into sleeve 23 or the anal canal.

Applicators 50 or 100 can include a mechanism that is sensitive to the pressing of finger hold 102 up against the external opening of the anus, and thereby providing the user tactical or auditory feedback of proper insertion position. For example, a click can be heard when applicator 50 or 100 is exposed to sufficient pressure from the front or the sides. Such pressure may also serves to collapse or otherwise disable rod 104 to prevent reuse and/or release plug 10 from applicator 50 or 100 and tells the user that applicator 50 or 100 is in far enough and that it can be withdrawn. Alternative feedback mechanisms can include a fluid filled balloon that is disposed between applicator 100 and plug 10 and emits a sound when exposed to pressure of a predetermined threshold. Tactile feedback can be provided by using a finger hold 102 design which facilitates tactile feedback. For example, finger hold 104 can include an exposed or thin membrane-covered window which transmits sensation to the operating finger such that the user can feel when plug 10 is fully inserted. Alternatively, finger hold 102 can be provided with elements (e.g. rubber rods) that project through the surface of finger hold 102 and can transmit tactile feedback from the exterior surface of finger hold 102 to the finger of the user.

Applicators 50 or 100 can be single use applicators and be fabricated from a biodegradable material (see example materials elsewhere herein) which can be recycled, safely landfilled or even flushed down the toilet.

Applicators 50 or 100 can include a reservoir for containing a gel, fluid or gas which can be pumped into plug 10 during or after insertion into the rectum, either manually or by pre-stored energy source.

Applicator 100 should have the ability to bend to accommodate the curvature of the anal canal, but yet stiff enough to not buckle or bend during the initial insertion procedure. The optimal stiffness based on experiments done by the inventors provides stiffness range of the applicator rod 104 so that when a preferably 50 to 250 gram weight, or more preferably 150-200 gram weight is applied to the end of a 50 mm long applicator rod 104, there is a tip displacement of around 10 mm.

For example, plug 10 designed as a collapsed balloon can be positioned via applicators 50 or 100 and inflated inside the rectum with fluid, gas, particles or a gel, including a reverse thermal gelation (RTG) gel such as Pluronic™ that will retain their shape at body temperature, or a hardening moldable compound such as VPS.

Plug 10 when filled with a fluid, gas, particles or gel can be configured so as to enable transfer of the filling material between regions of plug 10 which are then maintained in the proper internal geometry during movement of the anal canal and rectum. Optionally, plug 10 has within it one or more one way valves that prevent transferred fluid, gel or gas from moving backwards and deflating the acquired shape. Applicators 50 or 100 and plug 10 form a part of a system which is preferably co-packaged as a fecal incontinence kit. The kit can include a reusable applicator and several disposable plugs or it can include disposable applicator-plug pairs as well as instructions for use. The kit can contain a specific size of plug 10 and/or applicator 50 (e.g. small, medium or large) or it can include an assortment of sizes. Such a kit can include a disposal bag and/or a moist wipe or disposable gloves to help keep the plug insertion process as hygienic as possible even if not performed at home.

In an additional embodiment, an applicator which is designed for attaching to biasing cap 21 can be used with a plug 10 configuration which can be inserted into the anal canal without use of an inner or outer rod-type applicators such as those described above (applicators 50 and 100).

In such cases, plug 10 can include elements for stiffening stem portion 12 to thereby enable stem portion to be rigid enough for self insertion. It will be appreciated that such configurations can also be inserted into the anal canal without use of any applicator simply by holding plug 10 at biasing cap 21 and pushing it into the anal canal.

Several configurations for stiffening stem portion 12 are envisaged herein. Stem portion 12 can be a hollow tube which is filled with a gas, liquid or gel which stiffens stem portion 12. Following insertion into the anal canal, the gas, liquid or gel can be released from stem portion 12 allowing it to conform to anal canal anatomy and stretch to accommodate anal canal length.

A phase change material can also be used in stem portion 12 and optionally cap portion 14; the material can be stiff under room temperature and soft at body temperature. Plug 100 can be filled with such a material and deformed while molten (e.g. by stretching the plug from its ends) to as to form a more deliverable structure with reduced cap portion diameter when the material sets. Once in the body, the material melts and plug 100 assumes its natural configuration providing the anchoring and sealing necessary for treating fecal incontinence.

Figure 9A:
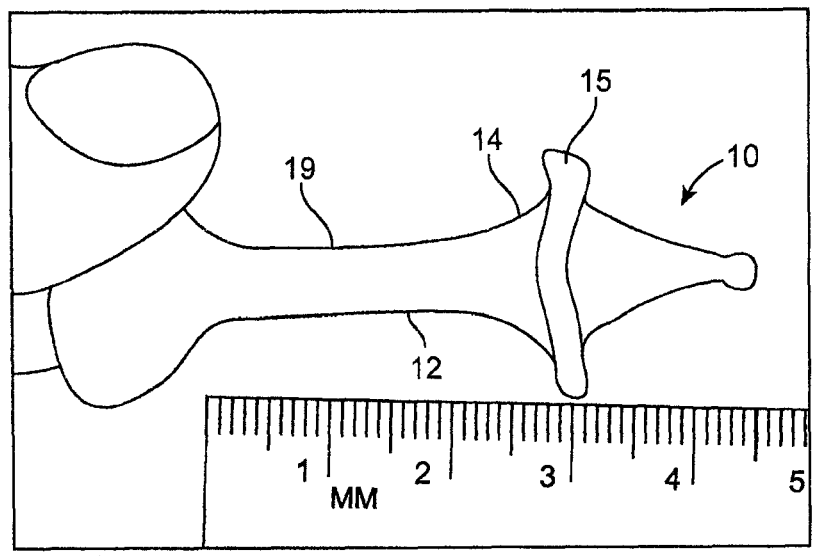
FIGS. 9A-B illustrate one configuration of the present plug which is introduced into the anal canal without an applicator as an elongated solid body. The plug core material melts at body temperature allowing the plug to resume its relaxed liquid-filled configuration. The plug is illustrated in its solid core (FIG. 9A) and liquid core (FIG. 9B) configurations.
Figure 9B:
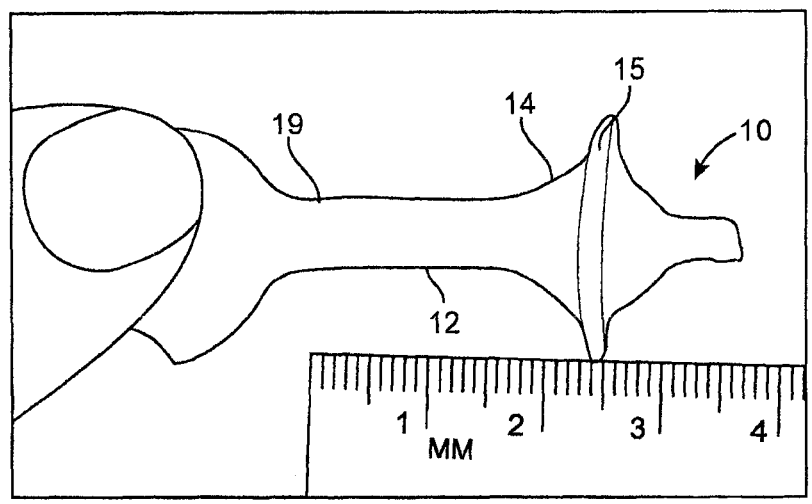

An example configuration of such a plug is shown in FIGS. 9A-B. External shell 19 is made of 0.4 nun thick silicone shore A 40 filled with molten Witespol™ hard fat. The plug is stretched and allowed to cool and harden while elongated as shown in FIG. 9A, thereby minimizing the cross sectional area of the plug to ease insertion and to allow disk 15 of cap portion 14 of the anchoring cap to sit above the top of the anal canal. Note that disk 15 is wavy and cap portion 14 elongated when the core of plug 10 is solid, thereby minimizing their diameters. The packaging of the plug can include a mechanism to keep the plug elongated during transport so even if the plug is exposed to temperatures above 37 deg C., when the plug re-cools it will maintain its elongated shape. Much like a candle design, stem portion 12 can include a central wick or mesh that helps provide stiffness and resistance to breakage of a hard and otherwise delicate thin elongated wax element.

The user pushes the plug in using a finger placed in the bottom of biasing element 21, much like a suppository is inserted into the anus. With this design, no applicator is needed. Biasing element 21 also shields the user's finger from touching the entrance to the anus. Shortly after insertion into the anus, the self-contained filling material melts and the plug resumes its relaxed shape, shown in FIG. 9B which allows disk 15 of cap portion 14 to seat properly in the lower rectum. Given that the plug is made of a liquid interior, the external shell can be made of relatively hard silicone, shore A 40+, and the overall plug is still well tolerated by the patient due to its squishy nature.

Example materials used to fill such a phase change plug include 70% poloxamer 188 (P188) and 30% propylene glycol, paraffin wax, polyester wax, solid fats such as polyglycerol ester of fatty acids (PGEFs for example: decaglycerol heptabehenate HB750 and hexaglycerol pentastearate PS500), beeswax, and Witepsol™ hard fats. The meltable material does not need to come into contact with the body and can be fully sealed inside plug 10.

Plug 10 can also be positioned without use of an applicator by configuring plug 10 with a hydratable solid core, which softens when hydrated. Biasing cap 21 in this embodiment is elastically connected to either stem portion 12 or directly and independently to cap portion 14. The latter option prevents the elasticity of biasing cap 21 from being affected by the stiffness of stem portion 12. Stem portion 12 includes a core which is made from a hydratable material such as PVA microporous foam or a desiccated hydrogel. Plug 10 can be elongated beyond its normal resting length and the rigidity of the dry core will keep it in that state until it is hydrated, thereby making plug 10 easier to insert into the anus. Cap portion 14 includes a top opening through which liquids can come in contact with the foam core or a self contained liquid ampoule can be punctured during or after the insertion process to soften the core. This opening ensures that once plug 10 is positioned within the anal canal, the top portion of the core wicks liquid from the lower rectal environment and into and along the length of the core thereby hydrating it and transforming it from rigid to soft. The final softness and elasticity of the core when wet can be configured to provide the proper mechanical properties that make the top portion of stem portion 12 an effective sealing element. Plug 10 of this configuration can be inserted in a manner similar to a stiff suppository by holding it at the bottom (biasing cap 21 region) and pushing it into the anal canal (with cap portion 14 protruding into the lower rectum). Once positioned, the core hydrates and softens within a minute or two making plug 10 softer and more elastic. The liquid that hydrates the core cannot leak out since the bottom and sides of stem portion 12 are not permeable to liquid. Alternatively, adjacent to the core within stem portion 12 is a liquid ampoule (not shown) that is burst upon entry of the plug into the anal canal and thereby softens core 25 within a preset time. Such a system is fully self contained and does not rely on any fluid transfer into or out of plug 10.

Alternatively, a coil core can also be used, in which case, compressing the coil for insertion provides rigidity from the stacked coils, following insertion, the coil relaxes and provides the elasticity necessary from stem portion 12. Alternatively, a stacked coil made of paper or a polymer can provide the necessary rigidity and be pulled out (while being unraveled) of the plug following insertion to allow for the desired plug softness and elasticity once fully inserted. As used herein the term "about" refers to .+−0.10%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following example.

EXAMPLES

Reference is now made to the following example, which together with the above description illustrate the invention in a non limiting fashion.

Example 1

Preformed Silicone Plug

A silicone plug as shaped like plug 10 in FIG. 3 having a Shore A value of 3 was fabricated using well known silicone molding techniques. The plug was loaded into a hollow applicator and was self administered into the anal canal of a continent male subject (as shown in FIGS. 4A-C and 5A-C). The subject carried the plug for 24 hours. Following the 24 hour period, the plug was ejected with defecation and collected.

Trace fecal material present on the plug indicated that feces managed to creep under one side of the cap structure of the plug but was stopped at the neck region of the plug (just under the cap). The stem was free of fecal matter indicating that the tightest seal occurs on the stem just below the cap.

The subject reported that the plug did not induce any perceived discomfort and remained in position throughout the experiment. The subject also reported that flatulence escaped around the plug without inducing any resistance to gas release or perceivable dislocation of the plug or leakage.

Example 2

Silicone Plug with Biasing Cap

Figure 10A:
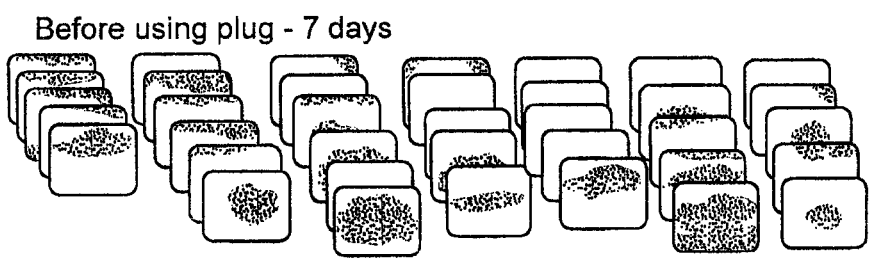
FIGS. 10A-B illustrate incontinence diapers of an incontinent subject prior to (FIG. 10A) and during (FIG. 10B) use of the present plug. One or more incontinence diapers were collected for each day of the testing period.
Figure 10B:
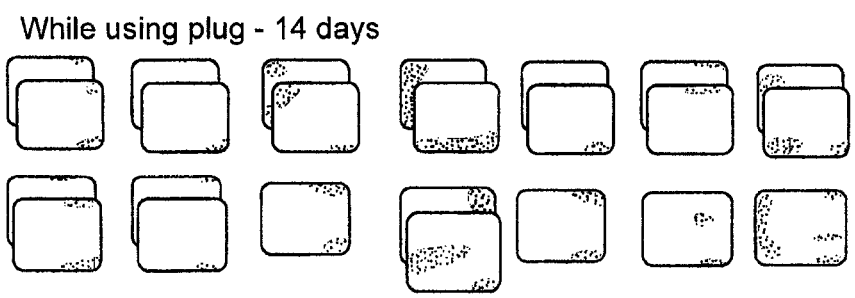

The plug design similar to that shown in FIG. 7 made of silicone shore A 3 and inner sleeve insert made from silicone shore A 20 was tested on a female patient diagnosed with severe fecal incontinence (Wexner or Cleveland Clinic Fecal Incontinence scale of 20 out of 20). On a daily basis over the course of two weeks the plug was self administered by the subject into the anal canal (in the manner shown in FIGS. 8A-C). The subject carried each plug for .about.12-24 hours over which time she also wore incontinence pads in order to trap any leaked solids or liquids. Following each bowel movement with occurred roughly every 12-24 hours, the pads and the plug were collected and analyzed (see FIG. 10A-B). The pads showed no signs of soiling or leakage indicating that the plug effectively prevented involuntary loss of fecal matter and hence restored full continence to this subject. In addition, the top of the cap portion showed evidence of staining with fecal matter while plug portions below the top surface of the cap portion were free of fecal matter as per the intended design of the plug. The subject reported that the plugs were very comfortable to the point of being imperceptible and were evacuated naturally, painlessly and effortlessly. Furthermore, the subject reported 1 to 2 normal and fuller bowel movements a day, as opposed to 5 to 6 episodes of bowel leakage prior to using the plug.

Example 3

Meltable Core Plug

The plug design similar to that shown in FIG. 9A-B with external shell 19 made of silicone shore A 40, filled through the bottom of stem portion 12 with molten Witespol™ solid fats that melts at 37 deg C., elongated while still molten by hanging a weight of 100 grams from it, allowed to cool and then sealed with a silicone RTV adhesive at the bottom of the stem portion 12 in order to keep the meltable core material fully contained in the external shell of plug 10. Plug 10 was tested on a female subject diagnosed with severe fecal incontinence (Wexner scale 20). On a daily basis over the course of a week the hollow plug was self administered by the subject into the anal canal in a manner similar to the insertion of a suppository. The subject carried each plug for .about.12-24 hours over which time she also wore incontinence pads in order to trap any leaked solids or liquids. Following each bowel movement with occurred roughly every 12-24 hours, the pads and the plug were collected and analyzed. The pads showed no signs of soiling or leakage indicating that the plug effectively prevented involuntary loss of fecal matter and hence restored full continence to this subject. In addition, the top of cap portion 14 showed evidence of staining with fecal matter while plug portions below the top surface of the cap portion were free of fecal matter as per the intended design of the plug. The plug as ejected with the core material in a liquid state due to the plug being exposed to body temperature. The subject reported that the plugs were very comfortable to the point of being imperceptible and were evacuated naturally, painlessly and effortlessly. Furthermore, the subject reported 1 to 2 normal and fuller bowel movements a day, as opposed to 5 or 6 episodes of bowel leakage prior to using the plug.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for treating fecal incontinence, the system comprising:
   (a) a plug including an anchoring element attached to a biasing element via an axially stretchable elongated body having an internal bore; and
   (b) an applicator including a finger hold connected to a rod which is removably insertable in said internal bore of the elongated body, said finger hold being spaced apart from said biasing element when said rod is fully inserted into said internal bore;
   said plug being configured such that when said plug is delivered through an anal canal via said applicator, an insertion force applied through said applicator stretches said axially stretchable elongated body on said rod such that said finger hold moves in a direction of said biasing element, wherein said axially stretchable elongated body stretches to bias said anchoring element downward against the rectal neck bottom when the biasing element engages the external anal surface.

2. The system of claim 1, wherein said anchoring element has a cupped or flat disc shape when outside the body.

3. The system of claim 1, wherein said anchoring element is configured to fold back when delivered through said anal canal.

4. The system of claim 1, wherein said anchoring element is a solid cupped or flat disc.

5. The system of claim 1, wherein said cupped or flat disc shape is adapted to fold back in response to direct contact between said anchoring element and a wall of said anal canal.

6. The system of claim 1, wherein said axially stretchable elongated body is supported by said rod when said rod is present in the internal bore.

7. The system of claim 1, wherein said finger hold moves away from said biasing element when said insertion force is released.

8. The system of claim 1, wherein said plug consists of a polymer having a Shore A hardness of less than 40.

9. The system of claim 1, wherein stretching of said axially stretchable elongated body enables said plug to accommodate anal canal length ranges from 2-5 cm.

* * * * *